United States Patent [19]

Deghenghi

[11] Patent Number: 5,795,957
[45] Date of Patent: Aug. 18, 1998

[54] POLYPEPTIDE COMPOUNDS CONTAINING D-2-ALKYLTRYPTOPHAN CAPABLE OF PROMOTING THE RELEASE OF GROWTH HORMONE

[76] Inventor: Romano Deghenghi, Chesaux Dessus B1, 1264 St. Cergue, Switzerland

[21] Appl. No.: 530,853

[22] Filed: Sep. 20, 1995

[30] Foreign Application Priority Data

Sep. 27, 1994 [IT] Italy ................... MI94A1954
Jun. 16, 1995 [IT] Italy ................... MI95A1293

[51] Int. Cl.$^6$ .................. A61K 38/00; A61K 38/02; C07K 5/00; C07K 7/00
[52] U.S. Cl. .................. 530/329; 530/300; 530/330; 514/16; 514/17
[58] Field of Search ................... 530/329, 330, 530/300; 514/17, 18, 16

[56] References Cited

U.S. PATENT DOCUMENTS

| | | | |
|---|---|---|---|
| 3,316,260 | 4/1967 | Shen et al. | |
| 4,223,019 | 9/1980 | Momany | 424/177 |
| 4,223,020 | 9/1980 | Momany | 424/177 |
| 4,223,021 | 9/1980 | Momany | 424/177 |
| 4,224,316 | 9/1980 | Momany | 424/177 |
| 4,226,857 | 10/1980 | Momany | 424/177 |
| 4,228,155 | 10/1980 | Momany | 424/177 |
| 4,228,156 | 10/1980 | Momany | 424/177 |
| 4,228,157 | 10/1980 | Momany | 424/177 |
| 4,228,158 | 10/1980 | Momany | 424/177 |
| 4,410,512 | 10/1983 | Bowers | 424/177 |
| 4,410,513 | 10/1983 | Momany | 424/177 |
| 4,411,890 | 10/1983 | Momany | 424/177 |
| 4,839,344 | 6/1989 | Bowers et al. | 514/16 |

FOREIGN PATENT DOCUMENTS

| | | | |
|---|---|---|---|
| 2016355 | 5/1990 | Canada. | |
| 0 083 864 | 7/1983 | European Pat. Off.. | |
| 0 203 031 | 11/1986 | European Pat. Off.. | |
| 0 401 507 | 4/1990 | European Pat. Off.. | |
| 88 09780 | 12/1988 | WIPO. | |
| 89/07110 | 8/1989 | WIPO. | |
| 91 18016 | 11/1991 | WIPO. | |
| 9118016 | 11/1991 | WIPO | C07K 7/20 |
| 94 07519 | 4/1994 | WIPO. | |

OTHER PUBLICATIONS

Deghenghi et al., *Life Sciences*, vol. 54, No. 18, pp. 1321–1328.

G. Tolis et al. "Growth Hormone Release in Thalassemic Patients by a New GH–Releasing Peptide Administered Intravenously or Orally". 75th Endocrine Society meeting, Las Vegas, NE, Jun. 9, 1993.

R. Deghenghi et al. "Structure–Activity Studies with Hexarelin and Related GH–Releasing Peptides" 3rd Intl. Pituitary Congress, Marina de Rey, CA, Jun. 13–15, 1993.

E. Arvat et al. "GH–Releasing Activity of Hexarelin, A New Wynthetic Hexapeptide, After Intravenous, Subcutaneous, Intranasal and Oral Administration In Man" Giornate Endocrinologiche Pisane, Pisa (Italy) Jun. 28–29, 1993.

L.K. Conley et al., Biological Potency of Hexarelin (EP23905) "Initial Studies on Oral Activity", presented 1992.

W.B. Wehrenerg et al., "Biological Potency of Hexarelin (EP23905), A New Growth Hormone–Releasing Peptide", presented 1992.

R. Deghenghi et al. "Hexarelin (EP23905)—A Sensitive Growth Hormone Releasing Peptide", presented in Milan, Italy, Sep. 1992.

L.K. Conley et al., "Studies on the Mechanism of Action of Hexarelin and GHRP–6", presented at International Symposium on Growth Hormone II, Basic Clinical Aspects, in Partpon Springs, Florida, Dec. 2–3, 1992.

B.P. Imbimbo et al., "Growth Hormone Releasing Activity of Hexarelin in Humans: A Dose–Responsive Study", presented at the International Symposium on Growth Hormone II, Basic Clinical Aspects, in Tarpon Springs, Florida, Dec. 3–6, 1992.

Silver et al., "Scleroderma, Fascities, and Eosinophillia Associated With the Igestion of Tryptophan", The New England Journal of Medicine, 332: No. 13, Mar. 29, 1990.

Karten et al., "Gonadotropin–Releasing Hormone Analog Design, Structure–Function Studies Toward the Development Agonists and Antagonists: Rationale and Perspective", Endocrine Reviews, 7(1):44–66(1986).

Yabe et al., "Synthesis and Biological Activity of LH–RH Analogs Substituted by Alkyltryptophans at Position 3", Chem Pharm. Bull, vol. 27, No. 8, (1979).

Pailthrope et al., Chenical Abstracts 79:400 (1973).

S. Majima, "E.W. Biologisches Verfahten der d–Tryptophandarstellans", Hoppe–Seyler's Z. Physiol Chem. 243:250 (1936).

*Primary Examiner*—Avis M. Davenport
*Attorney, Agent, or Firm*—Pennie & Edmonds LLP

[57] ABSTRACT

Novel peptides comprising D-2-alkyltryptophan, useful for promoting growth hormone release, compositions comprising such peptides and methods of using such compositions are described. In a preferred embodiment of the invention, the D-2-alkyl tryptophan is D-2-methyltryptophan.

12 Claims, No Drawings

POLYPEPTIDE COMPOUNDS CONTAINING D-2-ALKYLTRYPTOPHAN CAPABLE OF PROMOTING THE RELEASE OF GROWTH HORMONE

FIELD OF THE INVENTION

The present invention relates to oligopeptide compounds containing a D-2-alkyltryptophan amino acid and which are capable of releasing growth hormone from somatotropes, and are active by oral route.

BACKGROUND OF THE INVENTION

The increase of growth hormone ("GH") levels in mammals following the administration of compounds which induce GH release can lead to growth acceleration and muscular mass increase and, if sufficiently high GH levels are obtained following the administration, enhanced production of milk. Moreover, the increase of growth hormone levels in mammals can be achieved by administering known growth hormone release agents such as growth hormone release hormones ("GHRH").

The increase of growth hormone levels in mammals can also be obtained by administering growth hormone release peptides, some of which have been previously described, for example in U.S. Pat. Nos. 4,223,019, 4,223,020, 4,223,021, 4,224,316, 4,226,857, 4,228,155, 4,228,156, 4,228,157, 4,228,158, 4,410,512, 4,410,513, 4,411,890 and 4,839,344.

One of the more studied growth hormone release peptides is GHRP-6 (C. Y. Bowers et al., Endocrinology 114:1537 (1984) and has the formula His-D-Trp-Ala-Trp-D-Phe-Lys-$NH_2$. GHRP-6 releases growth hormone both in vitro and in vivo and is orally active in animals, including humans. Its molecular mechanism has been studied, as well as the molecular mechanism of its analogue heptapeptide GHRP-1 (Cheng et al., Endocrinology 124:2791 (1989); M. S. Akman et al., Endocrinology 132:1286 (1993)). It was found that contrary to natural GHRH, GHRP-1 and GHRP-6 act through different receptors for the release of GH and also via a different mechanism, which is independent from cAMP and which operates through other intracellular pathways, such as through the mobilization of calcium supplies and via a proteinkinase C (PKC)-dependent process (L. Bresson-Bépoldin and L. Dufy-Barbe, Cell. Calcium 15, 247 (1994)).

It has been found that the modification given by a single alkyl group in the 2-position of tryptophan (in its D-conformation), besides favorably increasing the stability of the Trp residue (R. Deghenghi, PCT Publication No. WO 91/18016 published Nov. 28, 1991 and R. Deghenghi et. al, Life Sciences 54, 1321 (1994)), is responsible for a change in the intracellular mechanisms which are independent from calcium, sometimes dependent on adenylcyclase and more similar to those of GHRH, as well as other peptide hormones. (James D. Watson et al., Molecular Biology of the Gene, 4th ed., The Benjamin/Cummings Publishing Company, Inc., Menlo Park, Calif., 1987, p. 60).

In view of the important effects that growth hormone releasing peptides can have on veterinary and human medicine, there remains a need for growth hormone releasing peptides that are more efficacious than those currently in existence, and as such, can be administered at a lower concentration and at a lower cost with fewer adverse health affects.

Therefore, rather simple, short-chained polypeptides capable of promoting growth hormone release, that are easily and conveniently prepared, as well as easily purified and formulated, and that are active when administered by oral route, are presently desired.

SUMMARY OF THE INVENTION

In a completely surprising manner it has now been found that the introduction of a D-2-alkyltryptophan (D-Mrp) in the oligopeptide of the GHRP series, modifies the intracellular mechanism of GH release. In addition, the introduction of D-2-Mrp into a GHRP results in a substantial increase of the activity of the adenylcyclase in the anterior pituitary glands, both of murine origin, and of human origin.

Another unexpected characteristic feature of the present invention is the very high potency of penta-, hexa-, and heptapeptides and the favorable oral activity/potency ratio of shorter-chained tetrapeptides of the series.

The oligopeptides of the present invention have the following formula:

A-D-Mrp-(Ala)$_n$-B-C and pharmaceutically acceptable salts thereof, wherein:

A is selected from the group consisting of any natural L-amino acid or its D-isomer, imidazolylacetyl, isonipectoyl, 4-aminobutyryl, 4-(aminomethyl)cyclohexanecarbonyl, Glu-Tyr-Ala-His, Tyr-Ala-His, Tyr-His, D-Thr-His, D-Ala, D-Thr, Tyr and Gly;

Mrp is 2-alkyltryptophan, wherein alkyl is selected from the group consisting of methyl, ethyl, n-propyl and isopropyl;

n=0–1;

B is selected from the group consisting of Trp, D-Trp, Phe and D-β-Nal; and

C is selected from the group consisting of $NH_2$, D-Phe-Lys-$NH_2$, Phe-Lys-$NH_2$, D-Trp-Lys-$NH_2$, D-Phe-Lys-Thr-$NH_2$, D-Phe-Lys-D-Thr-$NH_2$ and O-$C_1$–$C_3$ alkyl group; with the proviso that A is not His when B is L-Trp or D-Trp and when C is D-Phe-Lys-$NH_2$.

DETAILED DESCRIPTION OF THE INVENTION

The present invention lies in the discovery that different short-chained polypeptides which promote the release and increase of growth hormone levels in blood of animals, including humans, are characterized in that they comprise in the peptide chain thereof a D-isomer of 2-alkyltryptophan (D-2-Me-Trp or D-Mrp).

The polypeptides of the present invention are defined by the following formula:

A-D-Mrp-(Ala)$_n$-B-C and pharmaceutically acceptable salts thereof, wherein:

A is selected from the group consisting of any natural L-amino acid or its D-isomer, imidazolylacetyl, isonipectoyl, 4-aminobutyryl, 4-(aminomethyl)cyclohexanecarbonyl, Glu-Tyr-Ala-His, Tyr-Ala-His, Tyr-His, D-Thr-His, D-Ala, D-Thr, Tyr and Gly;

Mrp is 2-alkyltryptophan, wherein alkyl is selected from the group consisting from methyl, ethyl, n-propyl and isopropyl;

n=0–1;

B is selected from the group consisting of Trp, D-Trp, Phe and D-β-Nal; and

C is selected from the group consisting of $NH_2$, D-Phe-Lys-$NH_2$, Phe-Lys-$NH_2$, D-Trp-Lys-$NH_2$, D-Phe-Lys-Thr-$NH_2$, D-Phe-Lys-D-Thr-$NH_2$, and O-$C_1$–$C_3$ alkyl group;

with the proviso that A is not His when B is L-Trp or D-Trp and when C is D-Phe-Lys-NH$_2$.

Preferably, when B is Trp, then C is Phe-Lys-NH$_2$ or D-Phe-Lys-NH$_2$ and when B is Phe, then C is D-Trp-Lys-NH$_2$.

Most preferably, Mrp is 2-methyltryptophan.

The abbreviations used herein are as follows:
Gly=Glycine
Tyr=L-Tyrosine
Ile=L-Isoleucine
Glu=L-Glutamic Acid
Thr=L-Threonine
Phe=L-Phenylalanine
Ala=L-Alanine
Lys=L-Lysine
Asp=L-Aspartic Acid
Cys=L-Cysteine
Arg=L-Arginine
Gln=L-Glutamine
Pro=L-Proline
Leu=L-Leucine
Met=L-Methionine
Ser=L-Serine
Asn=L-Asparagine
His=L-Histidine
Trp=L-Tryptophan
Val=L-Valine
D-β-Nal=D-9-Naphthylalanine
INIP=Isonipecotyl
IMA=Imidazolylacetyl
GAB=4-aminobutyryl
Mrp=2-alkyltryptophan It is to be understood that when the notation "D-" immediately precedes one of the three-letter abbreviations for an amino acid as used herein and defined above, the amino acid immediately following the "D-" notation is the D-configuration. It is to be further understood that when the notation "D-" does not immediately precede one of the three-letter abbreviations for an amino acid as used herein and defined above, the amino acid is in the L-configuration.

According to the present invention, the alkyl group of Mrp is a $C_1$–$C_3$ alkyl group, i.e., methyl, ethyl, n-propyl or isopropyl. Preferably, the alkyl group of Mrp is methyl.

In addition, the peptides of the present invention can bear, on the C-terminus thereof, a $C_1$–$C_3$ alkyl ester, wherein alkyl is selected from the group consisting of methyl, ethyl, n-propyl and iso-propyl.

As used herein, "natural L-amino acid" refers to an amino acid bearing the L-configuration and being found in nature. Examples of natural L-amino acids include, but are not limited to L-tyrosine, L-isoleucine, L-glutamic acid, L-threonine, L-phenylalanine, L-alanine, L-lysine, L-aspartic acid, L-cysteine, L-arginine, L-glutamine, L-proline, L-leucine, L-methionine, L-serine, L-asparagine, L-histidine, L-tryptophan and L-valine.

As used herein, "therapeutically effective" means an amount or dose which, when administered to the animal including human, patient or subject, renders a benefit or an effect of increasing the level of cellular proteins such as hormones, or renders a benefit or an effect of treating or preventing an abnormal biological condition or disease.

As used herein, "EC$_{50}$" refers to the effective concentration for 50% of the peptides.

The most preferred growth hormone release compounds in the embodiment of the present invention are:
INIP-D-Mrp-D-Trp-Phe-Lys-NH$_2$;
INIP-D-Mrp-D-β-Nal-Phe-Lys-NH$_2$;
IMA-D-Mrp-D-Trp-Phe-Lys-NH$_2$;
IMA-D-Mrp-D-β-Nal-Phe-Lys-NH$_2$;
GAB-D-Mrp-D-Trp-Phe-Lys-NH$_2$;
GAB-D-Mrp-D-β-Nal-Phe-Lys-NH$_2$;
GAB-D-Mrp-D-β-Nal-NH$_2$;
GAB-D-Mrp-D-β-Nal-OC$_2$H$_5$;
imidazolylacetyl-D-Mrp-Ala-Trp-D-Phe-Lys-NH$_2$;
imidazolylacetyl-D-Mrp-D-Trp-Phe-Lys-NH$_2$;
imidazolylacetyl-D-Mrp-D-β-Nal-Phe-Lys-NH$_2$;
4-(aminomethyl)cyclohexanecarbonyl-D-Mrp-D-Trp-Phe-Lys-NH$_2$;
4-(aminomethyl)cyclohexanecarbonyl-D-Mrp-D-β-Nal-Phe-Lys-NH$_2$;
D-Ala-D-Mrp-Ala-Trp-D-Phe-Lys-NH$_2$;
D-Thr-D-Mrp-Ala-Trp-D-Phe-Lys-NH$_2$;
His-D-Mrp-Ala-Phe-D-Trp-Lys-NH$_2$;
His-D-Mrp-Ala-Trp-D-Phe-Lys-Thr-NH$_2$;
His-D-Mrp-Ala-Trp-D-Phe-Lys-D-Thr-NH$_2$;
Tyr-His-D-Mrp-Ala-Trp-D-Phe-LysNH$_2$;
His-D-Mrp-Ala-TrpNH$_2$;
D-Thr-His-D-Mrp-Ala-Trp-D-Phe-Lys-NH$_2$;
D-Thr-D-Mrp-Ala-TrpNH$_2$;
and pharmaceutically acceptable salts thereof, wherein Mrp is 2-methyltryptophan.

Pharmaceutically acceptable salts of the oligopeptide compounds of the present invention include but are not limited to organic or inorganic addition salts such as for example hydrochloride, hydrobromide, phosphate, sulfate, acetate, succinate, ascorbate, tartrate, gluconate, benzoate, malate and fumarate salts.

The polypeptide compounds according to the present invention can be synthesized according to the usual methods of peptide chemistry, both solid-phase and solution, or by means of the classical methods known in the art. The solid-phase synthesis starts from the C-terminal end of peptide. A suitable starting material can be prepared, for example, by attaching the required protected alpha-amino acid to a chloromethylated resin, a hydroxymethylated resin, a benzhydrylamine resin (BHA), or to a paramethylbenzhydrylamine resin (p-Me-BHA). As an example, an available chloromethylated resin is BIOBEADS® SX 1 by BioRad Laboratories, Richmond, Calif. The preparation of the hydroxymethyl resin is described by Bodansky et al., Chem. Ind. (London) 38, 15997 (1966). The BHA resin is described by Pietta and Marshall, Chem. Comm., 650 (1970) and is commercially available by Peninsula Laboratories Inc., Belmont, Calif.

After the starting attachment, the protecting group of the alpha-amino acid can be removed by means of different acid reagents, comprising trifluoroacetic acid (TFA) or hydrochloric acid (HCl) dissolved in organic solvents at room temperature. After the removal of the protecting group of the alpha-amino acid, the remaining protected amino acids can be coupled step by step in the desired order. Each protected amino acid can generally be reacted in excess of about three times using a suitable carboxyl activating group, such as dicyclohexylcarbodiimiide (DCC) or diisopropylcarbodiimide (DIC) dissolved, for example, in methylene chloride (CH$_2$Cl$_2$), dimethylformamide (DMF) or their mixtures. After the desired aminoacidic sequence has been completed, the desired peptide can be cleaved from the supporting resin by treatment with a reagent such as hydrogen fluoride (HF) which cleaves not only the peptide from the resin, but also the protecting groups of the lateral chains. When a chloromethylated resin or a hydroxymethylated resin is used, the treatment with HF leads to the formation of the acid peptide in free form. When a BHA or p-Me-BHA resin is used, treatment with HF directly leads to the formation of the amide peptide in free form.

The above discussed solid-phase procedure is known in the art and is described by Atherton and Sheppard, Solid Phase Peptide Synthesis (IRL Press, Oxford, 1989).

Some methods of solution-phase synthesis, which can be used to synthesize the peptide moieties of the present invention are detailed in Bodansky et al., Peptide Synthesis, 2nd edition, John Wiley & Sons, New York, N.Y. 1976 and in Jones, The Chemical Synthesis of Peptides (Clarendon Press, Oxford, 1994).

Compositions useful for releasing growth hormone in an animal, including a human, can comprise a peptide of the present invention or a pharmaceutically acceptable salt thereof, or combinations of peptides of the present invention or pharmaceutically acceptable salts thereof, optionally, in admixture with a carrier excipient, vehicle, diluent, matrix or delayed release coating. Examples of such carriers, excipients, vehicles and diluents, can be found in *Remington's Pharmaceutical Sciences*, Eighteenth Edition, A. R. Gennaro, Ed., Mack Publishing Company, Easton, Pa., 1990. The delayed release pharmaceutical forms, comprising bioerodible matrixes suitable for subcutaneous implant are particularly useful. Examples of these matrices are described in WO 92/22600 and WO 95/12629.

The compositions comprising the compounds of the present invention can be administered to animals, including humans, at a therapeutically effective dose which can be easily determined by one of skill in the art and which can vary according to the specie, age, sex and weight of the treated patient or subject. For example, in humans, when intravenously administered, the preferred dose falls in the range from about 0.1 µg to about 10 µg of total peptide per kg of body weight. When orally administered, typically higher amounts are necessary. For example, in humans for the oral administration, the dosage level is typically from about 30 µg to about 1000 µg of polypeptide per kg of body weight. The exact level can be easily determined empirically based on the above disclosure.

The compositions comprising the compounds of the present invention can be administered parenterally, but more conveniently intranasally or orally, or can be formulated in controlled release systems, such as biodegradable microcapsules, microspheres, subcutaneous implants and the like.

The following examples are presented by way of illustration and not by way of limitation on the scope of the invention.

EXAMPLE 1

Synthesis of GAB-D-Mrp-D-Trp-Phe-Lys-NH$_2$ (Mrp=2-methyltryptophan).

The synthesis of the title peptide was carried out by solid-phase with 9-fluorenylmethyloxycarbonyl (Fmoc)-protected amino acids involving resin preparation and assembly in a reactor column according to one of several methods known to those skilled in the art, as exemplified in "Solid phase peptide synthesis" by E. Atherton and R. C. Sheppard, IRL press at Oxford University press, 1989. The protected amino acids are Fmoc-Lys(Fmoc)-Opfp (Opfp= pentafluorophenyl ester), Fmoc-Phe-Opfp, Fmoc-D-Trp-Opfp, Fmoc-D-2-Me-Trp-Opfp and Fmoc-GAB-Opfp (GAB=gamma-aminobutyric). Alternatively, the use of Castro's reagents, benzotriazolyloxy-tris(dimethylamino) phosphonium(hexafluorophosphate) BOP and the pyridinium analog of BOP (PyBOP) (cfr. Le Nguyen and Castro (1988) in Peptide Chemistry 1987, p. 231–238; Protein Research Foundation Osaka; and Tetrahedron Letters 31, 205 (1990)) can be used advantageously as direct coupling reagents.

After cleavage and isolation, the title peptide was purified as its acetate salt. Purity (HPLC): 98%, MW (M+H$^+$)=764.3 (theoretical=763.9).

EXAMPLE 2

The following peptides were prepared according to the procedures described in Example 1, isolated as their TFA (triflouroacetate) salts and whenever needed, purified as their acetate salts:

INIP-D-Mrp-D-Trp-Phe-Lys-NH$_2$, purity (HPLC)= 99.0%, MW (M+H$^+$=790.4; theoretical=790.0);

INIP-D-Mrp-D-β-Nal-Phe-Lys-NH$_2$, purity (HPLC)= 96.5%, MW (M+H$^+$=801.4; theoretical=801.0);

IMA-D-Mrp-D-Trp-Phe-Lys-NH$_2$, purity (HPLC)= 99.2%, MW (M+H$^+$=786.5; theoretical=786.8);

IMA-D-Mrp-D-β-Nal-Phe-Lys-NH$_2$, purity (HPLC)= 97.3%, MW (M+H$^+$=798.3; theoretical=797.9);

GAB-D-Mrp-D-β-Nal-Phe-Lys-NH$_2$;

GAB-D-Mrp-D-β-Nal-NH$_2$;

4-(aminomethyl)cyclohexanecarbonyl-D-Mrp-D-Trp-Phe-Lys-NH$_2$, purity (HPLC)=99.0%, MW (M+H$^+$=818.5; theoretical=818.0);

4-(aminomethyl)cyclohexanecarbonyl-D-Mrp-D-β-Nal-Phe-Lys-NH$_2$, purity (HPLC)=96.9%, MW (M+H$^+$=829.5; theoretical=829.1);

D-Ala-D-Mrp-Ala-Trp-D-Phe-Lys-NH$_2$, purity (HPLC)= 99.3%, MW (M+H$^+$=821.3; theoretical=821.9);

D-Thr-D-Mrp-Ala-Trp-D-Phe-Lys-NH$_2$, purity (HPLC)= 98.0%, MW (M+H$^+$=851.5; theoretical=852.0);

His-D-Mrp-Ala-Phe-D-Trp-Lys-NH$_2$, purity (HPLC)= >98.6%, MW (M+H$^+$=887.4; theoretical=888.0);

Tyr-His-D-Mrp-Ala-Trp-D-Phe-Lys-NH$_2$, purity (HPLC) =96.8%, MW (M+H$^+$=1050.2; theoretical=1050.2);

His-D-Mrp-Ala-Trp-NH$_2$, purity (HPLC)=99.8%, MW (M+H$^+$=612.3; theoretical=612.7);

D-Thr-D-Mrp-Ala-Trp-NH$_2$, purity (HPLC)=97.5%, MW (M+H$^+$=576.5; theoretical=576.6);

His-D-Mrp-Ala-Trp-D-Phe-Lys-Thr-NH$_2$;

His-D-Mrp-Ala-Trp-D-Phe-Lys-D-Thr-NH$_2$;

D-Thr-His-D-Mrp-Ala-Trp-D-Phe-Lys-NH$_2$; and imidazolylacetyl-D-Mrp-Ala-Trp-D-Phe-Lys-NH$_2$, wherein Mrp is 2-methyltryptophan, and INIP, IMA and GAB are as defined above.

EXAMPLE 3

Synthesis of GAB-D-Mrp-D-β-Nal-OC$_2$H$_5$.

The peptide GAB-D-Mrp-D-β-Nal-OC$_2$H$_5$, bearing an ethyl ester in the C-terminal position, was synthesized via solution-phase synthesis according to conventional methods such as those described in of Bodansky et al., Peptide Synthesis, 2nd edition, John Wiley & Sons, New York, N.Y. 1976 and Jones, The Chemical Synthesis of Peptides (Clarendon Press, Oxford, 1994), wherein the starting material used in the synthesis of the title compound was D-β-naphthylalanine ethyl ester.

EXAMPLE 4

Biological activity

In vivo activity of these compounds was determined in ten day-rats, which were subcutaneously injected (s.c.) with a dose of 300 μg/kg or with different doses in dose-response studies, according to the procedure as described in Deghenghi et. al. Life Sciences 54, 1321 (1994). The results are shown in Table 1, below. The released GH was measured 15 minutes following compound administration.

The peptide known as HEXARELIN and having the structure His-D-Mrp-Ala-Trp-D-Phe-Lys-NH₂ is included in the table as a reference standard.

The GHRP-2 (reference standard) has the structure D-Ala-D-β-Nal-Ala-Trp-D-Phe-Lys-NH₂ (Chen and Clarke, J. Neuroend. 7, 179 (1995).

TABLE 1

| Peptide | Dose μg/kg s.c. | GH control (ng/ml) | GH released (ng/ml) |
|---|---|---|---|
| His—D-Mrp—Ala—Trp—D-Phe—Lys—Thr—NH₂ | 300 | 31 ± 8 | 176 ± 20 |
| His—D-Mrp—Ala—Trp—D-Phe—Lys—NH₂ | 300 | 14.7 ± 1.9 | 104.2 ± 13.1 |
| His—D-Mrp—Ala—Trp—D-Phe—Lys—D-Thr—NH₂ | 300 | 31 ± 8 | 169 ± 27 |
| D-Thr—D-Mrp—Ala—Trp—D-Phe—Lys—NH₂ | 300 | 31 ± 8 | 266 ± 20 |
| D-Thr—His—D-Mrp—Ala—Trp—D-Phe—Lys—NH₂ | 300 | 31 ± 8 | 86 ± 19 |
| D-Ala—D-Mrp—Ala—Trp—D-Phe—Lys—NH₂ | 40 | 34 ± 1 | 200 ± 20 |
| D-Ala—D-Mrp—Ala—Trp—D-Phe—Lys—NH₂ | 320 | 34 ± 1 | 251 ± 32 |
| His—D-Mrp—Ala—Trp—NH₂ | 5000 | 69 ± 14 | 124 ± 37 |
| imidazolylacetyl—D-Mrp—Ala—Trp—D-Phe—Lys—NH₂ | 300 | 20 ± 3 | 159 ± 27 |
| imidazolylacetyl—D-Mrp—D-Trp—Phe—Lys—NH₂ | 300 | 14.7 ± 1.9 | 60.3 ± 8.1 |
| imidazolylacetyl—D-Mrp—D-β-Nal—Phe—Lys—NH₂ | 300 | 14.7 ± 1.9 | 56.0 ± 12.4 |
| INIP—D-Mrp—D-Trp—Phe—Lys—NH₂ | 300 | 15 | 155 |
| INIP—D-Mrp—D-Trp—Phe—Lys—NH₂ | 300 | 14.7 ± 1.9 | 119.5 ± 18.6 |
| INIP—D-Mrp—D-β-Nal—Phe—Lys—NH₂ | 300 | 15 | 150 |
| INIP—D-Mrp—D-β-Nal—Phe—Lys—NH₂ | 300 | 14.7 ± 1.9 | 125.9 ± 13.0 |
| 4-(aminomethyl)cyclohexanecarbonyl—D-Mrp—D-Trp—Phe—Lys—NH₂ | 300 | 14.7 ± 1.9 | 111.8 ± 24.6 |
| GAB—D-Mrp—D-Trp—Phe—Lys—NH₂ | 300 | 10 | 110 |
| GAB—D-Mrp—D-Trp—Phe—Lys—NH₂ | 300 | 14.7 ± 1.9 | 172.8 ± 15.8 |
| GAB—D-Mrp—D-β-Nal—Phe—Lys—NH₂ | 300 | 14.7 ± 1.9 | 198.0 ± 13.2 |
| (GHRP-2) | 300 | 10 | 98.6 |
| (GHRP-2) | 300 | 14.7 ± 1.9 | 154.4 ± 18.5 |

In vitro measurements of adenylcyclase activity were determined in anterior pituitary gland cells from rats weighing 150 g and showed a 30% increase compared with the baseline with $EC_{50}=0.23$ nM for the peptide D-Ala-D-Mrp-Ala-Trp-D-Phe-Lys-NH₂, whereas GHRP-6 (His-D-Trp-Ala-Trp-D-Phe-Lys-NH₂) resulted inactive.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited and the entire disclosures of which are incorporated herein by reference.

What is claimed is:

1. A peptide of formula:

A-D-Mrp-(Ala)ₙ-B-C and pharmaceutically acceptable salts thereof, wherein:

A is selected from the group consisting of any single natural L-amino acid, any single D-isomer of an amino acid, imidazolylacetyl, isonipectoyl, 4-aminobutyryl, 4-(aminomethyl)cyclohexanecarbonyl, Glu-Tyr-Ala-His, Tyr-Ala-His, Tyr-His, and D-Thr-His;

Mrp is 2-alkyltryptophan, wherein alkyl is selected from the group consisting from methyl, ethyl, n-propyl and iso-propyl;

n=0 or 1;

B is selected from the group consisting of Trp, D-Trp, Phe and D-β-Nal; and

C is selected from the group consisting of NH₂, D-Phe-Lys-NH₂, Phe-Lys-NH₂, D-Trp-Lys-NH₂, D-Phe-Lys-Thr-NH₂, D-Phe-Lys-D-Thr-NH₂ and O-C₁-C₃ alkyl group;

with the proviso that A is not His when B is L-Trp or D-Trp and when C is D-Phe-Lys-NH₂.

2. The peptide according to claim 1, wherein Mrp is 2-methyltryptophan.

3. The peptide according to claim 1, wherein A is selected from the group consisting of imidazolylacetyl, isonipecotyl, 4-aminobutyryl, D-Ala, D-Thr and Tyr.

4. The peptide according to claim 1, wherein C is selected from the group consisting of Phe-Lys-NH₂, D-Trp-Lys-NH₂ and NH₂.

5. The peptide according to claim 1, selected from the group consisting of:

INIP-D-Mrp-D-Trp-Phe-Lys-NH₂;

INIP-D-Mrp-D-β-Nal-Phe-Lys-NH₂;

IMA-D-Mrp-D-Trp-Phe-Lys-NH₂;

IMA-D-Mrp-D-β-Nal-Phe-Lys-NH₂;

GAB-D-Mrp-D-Trp-Phe-Lys-NH₂;

GAB-D-Mrp-D-β-Nal-Phe-Lys-NH₂;

GAB-D-Mrp-D-β-Nal-NH₂;

GAB-D-Mrp-D-β-Nal-OC₂H₅;

imidazolylacetyl-D-Mrp-Ala-Trp-D-Phe-Lys-NH₂;

imidazolylacetyl-D-Mrp-D-Trp-Phe-Lys-NH₂;

imidazolylacetyl-D-Mrp-D-β-Nal-Phe-Lys-NH₂;

4-(aminomethyl)cyclohexanecarbonyl-D-Mrp-D-Trp-Phe-Lys-NH₂;

4-(aminomethyl)cyclohexanecarbonyl-D-Mrp-D-β-Nal-Phe-Lys-NH₂;

D-Ala-D-Mrp-Ala-Trp-D-Phe-Lys-NH₂;

D-Thr-D-Mrp-Ala-Trp-D-Phe-Lys-NH₂;

His-D-Mrp-Ala-Phe-D-Trp-Lys-NH₂;

His-D-Mrp-Ala-Trp-D-Phe-Lys-Thr-NH₂;

His-D-Mrp-Ala-Trp-D-Phe-Lys-D-Thr-NH$_2$;
Tyr-His-D-Mrp-Ala-Trp-D-Phe-LysNH$_2$;
His-D-Mrp-Ala-TrpNH$_2$;
D-Thr-His-D-Mrp-Ala-Trp-D-Phe-Lys-NH$_2$;
D-Thr-D-Mrp-Ala-TrpNH$_2$;
and pharmaceutically acceptable salts thereof, wherein Mrp is 2-methyltryptophan.

6. A method for promoting the release of growth hormone in an animal, comprising administering to said animal a therapeutically effective amount of a composition comprising a peptide of any one of claims 1–5.

7. The method according to claim 6, wherein the animal is a human.

8. A method for promoting the increase of the intracellular activity of adenylcylase in an animal, comprising administering to said animal a therapeutically effective amount of a peptide of claim 5.

9. A pharmaceutical composition comprising a therapeutically effect amount of a peptide of any one of claims 1–5, optionally in admixture with a carrier or an excipient.

10. The composition according to claim 9 wherein said composition is in the form of a composition for parenteral, intranasal, oral, controlled release administration, subcutaneous implants.

11. The peptide according to claim 1, selected from the group consisting of:
INIP-D-Mrp-D-Trp-Phe-Lys-NH$_2$;
INIP-D-Mrp-D-β-Nal-Phe-Lys-NH$_2$;
4-(aminomethyl)cyclohexanecarbonyl-D-Mrp-D-Trp-Phe-Lys-NH$_2$;
His-D-Mrp-Ala-Trp-NH$_2$; and pharmaceutically acceptable salts thereof, wherein Mrp is 2-methyltryptophan.

12. The peptide according to claim 1, selected from the group consisting of:
GAB-D-Mrp-D-Trp-Phe-Lys-NH$_2$;
GAB-D-Mrp-D-β-Nal-Phe-Lys-NH$_2$;
imidazolylacetyl-D-Mrp-Ala-Trp-D-Phe-Lys-NH$_2$;
D-Ala-D-Mrp-Ala-Trp-D-Phe-Lys-NH$_2$;
D-Thr-D-Mrp-Ala-Trp-D-Phe-Lys-NH$_2$;
His-D-Mrp-Ala-Trp-D-Phe-Lys-Thr-NH$_2$;
His-D-Mrp-Ala-Trp-D-Phe-Lys-D-Thr-NH$_2$; and
pharmaceutically acceptable salts thereof, wherein Mrp is 2-methyltryptophan.

* * * * *